(12) United States Patent
O'Rourke et al.

(10) Patent No.: US 12,211,595 B2
(45) Date of Patent: Jan. 28, 2025

(54) SYSTEM AND METHOD FOR IDENTIFYING CANDIDATES FOR CLINICAL TRIALS

(71) Applicant: ObjectiveHealth, Inc., Franklin, TN (US)

(72) Inventors: Joshua O'Rourke, Hendersonville, TN (US); Matthew Wallace, Franklin, TN (US); Donald Lazas, Nashville, TN (US); Colleen Hoke, Brentwood, TN (US)

(73) Assignee: ObjectiveHealth, Inc., Franklin, TN (US)

( * ) Notice: Subject to any disclaimer, the term of this patent is extended or adjusted under 35 U.S.C. 154(b) by 81 days.

(21) Appl. No.: 17/826,476

(22) Filed: May 27, 2022

(65) Prior Publication Data

US 2022/0383995 A1    Dec. 1, 2022

Related U.S. Application Data

(60) Provisional application No. 63/194,630, filed on May 28, 2021.

(51) Int. Cl.
*G16H 10/20* (2018.01)
*G16H 15/00* (2018.01)
(Continued)

(52) U.S. Cl.
CPC ............. *G16H 10/20* (2018.01); *G16H 15/00* (2018.01); *G16H 40/20* (2018.01); *G16H 50/20* (2018.01); *G16H 50/30* (2018.01); *G16H 50/70* (2018.01)

(58) Field of Classification Search
CPC ........ G16H 50/20; G16H 50/70; G16H 50/30; G16H 10/20; G16H 15/00; G06F 16/24578
See application file for complete search history.

(56) References Cited

U.S. PATENT DOCUMENTS

2007/0294110 A1\*  12/2007  Settimi .................. G16H 10/60
                                                        705/3
2008/0114616 A1\*  5/2008  Ferguson ............... G06Q 10/10
                                                        705/2
(Continued)

OTHER PUBLICATIONS

Pressler TR, Yen PY, Ding J, Liu J, Embi PJ, Payne PR. Computational challenges and human factors influencing the design and use of clinical research participant eligibility pre-screening tools. BMC Med Inform Decis Mak. May 30, 2012;12:47. doi: 10.1186/1472-6947-12-47. PMID: 22646313 (Year: 2012).\*

(Continued)

*Primary Examiner* — Joseph D Burgess
(74) *Attorney, Agent, or Firm* — Nelson Mullins Riley & Scarborough LLP; Anthony A. Laurentano (57) ABSTRACT

A system and method for identifying a plurality of candidates for one or more clinical trials comprising receiving health related data associated with each of the plurality of candidates, applying a predictive risk model to the health related data and for generating and assigning a risk score to each of the plurality of candidates based on a selected condition and then ranking each of the plurality of candidates based on the risk score, and generating a similarity score for each of the candidates having an assigned risk score higher than the threshold risk score with a matching machine learning technique. The similarity score is indicative of a similarity between each of the plurality of candidates and one or more participants in the one or more clinical trials.

29 Claims, 6 Drawing Sheets

(51) Int. Cl.
    *G16H 40/20*     (2018.01)
    *G16H 50/20*     (2018.01)
    *G16H 50/30*     (2018.01)
    *G16H 50/70*     (2018.01)

(56) References Cited

U.S. PATENT DOCUMENTS

| | | | |
|---|---|---|---|
| 2018/0301205 A1* | 10/2018 | Mao | G16H 10/20 |
| 2020/0020421 A1* | 1/2020 | Dimitrova | G16B 30/20 |
| 2020/0243168 A1 | 7/2020 | Clark et al. | |
| 2020/0258599 A1* | 8/2020 | Clark | G06N 20/00 |
| 2022/0084662 A1* | 3/2022 | Das | A61B 5/02055 |
| 2022/0261668 A1* | 8/2022 | Stumpe | G06F 16/284 |

OTHER PUBLICATIONS

International Search Report and Written Opinion, PCT/US2022/031276, dated Sep. 22, 2022, 11 pages.

\* cited by examiner

Prioritized View

| Patient ID | Name | Status | Risk Score |
|---|---|---|---|
| 213456 | J. Doe | Screen Ready | 90% |
| 312456 | A. Smith | Screen Ready | 85% |
| 345671 | C. Brown | Recruitment | 85% |
| 987453 | M. Smith | Recruitment | 75% |
| 239753 | I. Wilson | Screening | 85% |
| 654234 | F. Johnson | Never Eligible | 30% |

FIG. 4A

Schedule View

| Patient ID | Name | Appointment | Risk Score |
|---|---|---|---|
| 939027 | S. Crow | 2022-04-01 1:00 PM | 66% |
| 161365 | J. Peters | 2022-04-01 1:30 PM | 85% |
| 306631 | A. Lane | 2022-04-01 2:00 PM | 88% |
| 440127 | C. McCann | 2022-04-01 2:30 PM | 53% |
| 492965 | B. Bower | 2022-04-01 3:00 PM | 26% |
| 932156 | J. Smith | 2022-04-01 3:30 PM | 13% |

Table 150:

| Patient ID | Name | Study | Score |
|---|---|---|---|
| 213456 | J. Doe | Study A | 89% |
| 312456 | A. Smith | Study C | 69% |
| 345671 | C. Brown | Study A | 64% |
| 987453 | M. Smith | Study B | 59% |
| 239753 | I. Wilson | Study B | 53% |
| 654234 | F. Johnson | Study C | 30% |

Table 160:

| Study | Score |
|---|---|
| Study A | 89% |
| Study B | 51% |
| Study C | 12% |

FIG. 6

SYSTEM AND METHOD FOR IDENTIFYING CANDIDATES FOR CLINICAL TRIALS

RELATED APPLICATION

The present application claims priority to U.S. provisional patent application Ser. No. 63/194,630, filed on May 28, 2021, and entitled System and Method For Pre-Screening Patients For Clinical Trials, the contents of which are herein incorporated by reference.

BACKGROUND OF THE INVENTION

While it is common in the art to manually pre-screen candidates for clinical trials within research organizations, the conventional systems have attempted to optimize such processes through computerized automation. Many of these conventional systems are configured for extracting inclusion/exclusion criteria from clinical trial descriptions through natural language processing (NLP) or rules-based techniques and then applying the extracted criteria to electronic health record databases in order to search for and hence find potential clinical trial candidates.

While prior art systems are interesting and useful in their ability to directly or indirectly extract rules from clinical trial descriptions, these systems are fundamentally limited in that the associated rules are designed to be read by humans rather than being automatically evaluated by associated computing systems. Without interpretation from a skilled clinician, these criteria often lack the specificity and detail required to correctly identify true candidates without a high margin of error. Further, these conventional systems are often removed from and hence do not communicate with the clinical workflow in which they would be used and typically neglect the prioritization and ranking of patient candidates.

The foregoing limitations of the prior art systems can lead to a number of significant drawbacks. These drawbacks include the lack of domain knowledge required to interpret clinical information embedded in the inclusion/exclusion criteria. The conventional systems also suffer from high error rates due to the specificity of the criteria, incompleteness of the candidate's medical history, and inability to transform the criteria into discrete rules that can be utilized by computerized filtering and matching techniques. The conventional systems also do not attempt to generalize criteria across multiple clinical trials for the same chronic disease, such that patient candidates cannot be efficiently screened for factors relevant to their condition. Further, conventional systems do not apply a risk stratification technique to the candidate data and then stratify the patients in order to identify whether they have an undiagnosed condition that may qualify them for clinical trials relevant to their condition. Also, consequentially, the conventional systems ignore clinical workflows and procedures typically embedded in the screening process that may help identify undiagnosed conditions relevant to a particular clinical trial.

SUMMARY OF THE INVENTION

The present invention is directed to a computerized system and method for identifying, risk stratifying, and prioritizing potential clinical trial participants or candidates from one or more databases of electronic health information and then matching them to the most relevant clinical trial based on their similarity to other subjects that who have successfully enrolled in, been assigned, or are participating in the clinical trial. The system and method involve obtaining a clinical summary for a candidate in real-time as events are scheduled in the electronic health record system and using this information to risk stratify the patient and use inference data to score the patient for one or more diseases for which a relevant clinical trial is being conducted. The candidates are then prioritized and moved through an automated selection process (e.g., workflow) where they can be efficiently matched to a relevant clinical trial based on their similarity to other participants who have successfully enrolled in the trial.

The present invention is directed to a candidate identification system for identifying a plurality of candidates for one or more clinical trials. The system includes one or more data sources for providing health related data associated with each of the plurality of candidates, an integration engine for integrating the health related data to form normalized health related data, a data storage element for storing the normalized health related data, and a risk stratification unit for applying a predictive risk model to the normalized health related data and for generating and assigning a risk score to each of the plurality of candidates based on a selected condition and then ranking each of the plurality of candidates based on the risk score. The risk stratification unit is configured to compare the assigned risk scores with a threshold risk score. The system further includes a matching unit for employing one or more matching machine learning techniques to generate a similarity score for each of the plurality of candidates having the assigned risk score higher than the threshold risk score. The similarity score is indicative of a similarity between each of the plurality of candidates and one or more participants in the one or more clinical trials.

The system can optionally include one or more of a workflow rules unit for applying one or more workflow rules to each of the plurality of candidates, and an evaluation unit for providing evaluation data about each of the plurality of candidates. The matching unit matches each of the candidates to one or more clinical trials based on the risk score data and optionally on the evaluation data. The matching unit further matches each of the candidates to one or more clinical trials based on the health related data. Further, the evaluation unit determines, based on the assigned risk scores of each of the candidates, which of the candidates are to be evaluated. The matching unit ranks the plurality of candidates based on the similarity scores of the plurality of candidates. The risk score generated by the risk stratification unit is indicative of whether the candidate is at-risk for one or more health conditions or has a propensity for complications with a diagnosed condition.

The system can further optionally include one or more of an event router for routing the normalized health related data from the integration engine to the data storage element, a plurality of service modules each of which is configured for processing a different portion of the normalized health related data stored in the data storage element, and a query unit for generating a query and then searching the normalized health related data stored in the data storage element for one or more portions of the normalized health related data that satisfy the query. The plurality of service modules can be configured for processing a different portion of the normalized health related data stored in the data storage element. The service modules can include two or more of a scheduling service module for processing a scheduling event data portion of the normalized health related data; a clinical summary service module for processing a clinical summary event data portion of the normalized health related data; a clinical administration service module for processing an administration event data portion of the normalized health related data; and a clinical result service module for processing a test result portion of the normalized health related data. The scheduling service module generates a request for a query to a query unit based on the scheduling event data portion of the normalized health related data, and in response to the request, the query unit requests updated clinical summary event data from the one or more data sources.

The present invention is also directed to a method for identifying a plurality of candidates for one or more clinical trials, comprising receiving health related data associated with each of the plurality of candidates, applying a predictive risk model to the health related data and for generating and assigning a risk score to each of the plurality of candidates based on a selected condition and then ranking each of the plurality of candidates based on the risk score, and generating a similarity score for each of the candidates having an assigned risk score higher than the threshold risk score with a matching machine learning technique. The similarity score is indicative of a similarity between each of the plurality of candidates and one or more participants in the one or more clinical trials. The health related data can include scheduling data indicative of a medical appointment and clinical summary data indicative of medical history data of each of the plurality of candidates. The risk score can be generated based on one or more of the scheduling data and the medical history data. The risk score assigned to each of the plurality of candidates is compared with a threshold level risk score, and the candidates with risk scores above the threshold level are identified as being possible clinical trial candidates.

The method of the present invention an also optionally include one or more of applying one or more workflow rules to each of the plurality of candidates, or receiving evaluation data about one or more of the plurality of candidates having the assigned risk score above the threshold risk score level, wherein the evaluation includes additional health related data. The method includes matching each of the candidates to one or more clinical trials based on the risk score data and optionally, additionally, on the evaluation data. The method further includes determining, based on the assigned risk scores of each of the candidates, which of the candidates are to be evaluated. The candidates can be ranked based on the similarity scores. The risk score is indicative of whether the candidate is at-risk for one or more health conditions or has a propensity for complications with a diagnosed condition.

The method can also include generating the similarity score for each of the identified candidates based on the risk score and the evaluation data. Further, the method includes scheduling each of the matched candidates for further evaluation.

The present invention is also directed to a non-transitory, computer readable medium comprising computer program instructions tangibly stored on the computer readable medium, wherein the computer program instructions are executable by at least one computer processor to perform a method, where the method includes receiving health related data associated with each of the plurality of candidates, applying a predictive risk model to the health related data and for generating and assigning a risk score to each of the plurality of candidates based on a selected condition and then ranking each of the plurality of candidates based on the risk score, and generating a similarity score for each of the candidates having an assigned risk score higher than the threshold risk score with a matching machine learning technique. The similarity score is indicative of a similarity between each of the plurality of candidates and one or more participants in the one or more clinical trials. The health related data includes scheduling data indicative of a medical appointment and clinical summary data indicative of medical history data of each of the plurality of candidates. The risk score is generated based on at least the scheduling data and the medical history data.

The computer readable medium can also include instructions for comparing the risk score assigned to each of the plurality of candidates with a threshold level risk score and identifying the candidates with risk scores above the threshold level. The computer readable medium can also include, optionally, instructions for applying one or more workflow rules to each of the plurality of candidates or receiving evaluation data about each of the plurality of candidates, wherein the evaluation includes additional health related data.

The computer readable medium further includes instructions for matching each of the candidates to one or more clinical trials based on the evaluation data and based on the risk score data, and determining, based on the assigned risk scores of each of the candidates, which of the candidates are to be evaluated. The computer readable medium can also include instructions for ranking each of the plurality of candidates based on the similarity scores of the plurality of candidates. The risk score is indicative of whether the candidate is at-risk for one or more health conditions or has a propensity for complications with a diagnosed condition. The computer readable medium can also include instructions for generating the similarity score for each of the identified candidates based on the risk score and the evaluation data, and scheduling each of the matched candidates for further evaluation.

BRIEF DESCRIPTION OF THE DRAWINGS

These and other features and advantages of the present invention will be more fully understood by reference to the following detailed description in conjunction with the attached drawings in which like reference numerals refer to like elements throughout the different views. The drawings illustrate principals of the invention and, although not to scale, show relative dimensions.

DETAILED DESCRIPTION

Rather than focus on identifying potential clinical trial candidates based solely on the inclusion/exclusion criteria for a specific trial, the present invention generalizes the search for patient candidates for clinical trials by risk stratifying and prioritizing the candidates based on their likelihood of having an undiagnosed or undocumented disease or their propensity for recurring complications associated with an existing disease or condition. The present invention is also directed to a method for automating the movement of a patient candidate through the recruitment, evaluation, intervention, and screening process and then matching the candidate to one or more clinical trials based on their similarity to other patients that have successfully screened for those clinical trials.

As such, the candidate identification system of the present invention can be employed to pre-screen potential candidates for a clinical trial by receiving scheduling information directly from a primary or specialty healthcare provider in real-time in order to identify potential candidates for clinical trials as they are being evaluated by their provider. As such, the system of the present invention can receive a summary of the candidate's medical history from the healthcare provider as they are scheduled for appointments so that the candidate can be risk stratified prior to being seen by the healthcare provider. The candidates can also be risk stratified after the conclusion of the appointment as the medical information of the candidate is updated. The candidates can be risk stratified against evidence-based physiologic and molecular biomarkers in order to identify undiagnosed or undocumented chronic conditions and match them to related or relevant clinical trials. The system can also determine a workflow state at which the candidate should be placed based on completeness of an associated medical history, completion and results of pre-screening procedures, risk stratification scores and ranked position, and exclusion criteria. The system can prioritize and rank the order in which the candidates are presented to a system user such that the highest risk candidates are screened before those with lower risks while taking into consideration their current state in the screening workflow process, as well as their similarity to other candidates that have qualified for selected clinical trials. The system can be configured to present to a system user a list of potential candidates ranked according to their risk of having a condition and their current state in the pre-screening workflow, as well as presenting a summary of a medical history of the candidates including their risk score and current state in the recruitment, evaluation, and preparatory-to-research workflow.

An advantage of the present invention is that a summary of a medical history of the candidate is received as patients are scheduled for, arrive at, and complete appointments with their healthcare provider so that they can be identified as a potential candidate for a clinical trial, in real-time, as they are being seen by their healthcare provider. The candidates are assigned risk scores and then are stratified based on the risk scores (e.g., risk stratified) according to evidence-based physiological and molecular biomarkers to identify undiagnosed or undocumented conditions which may qualify or disqualify them for a clinical trial. The patient risk stratification, both risk scores and ranking, can be re-evaluated by the system as new health related information is received from the healthcare providers of the candidate (e.g., medical record data) or pre-screening workflow so that new clinical trial candidate can be identified as more health related information is obtained. The patients can also be automatically moved through the pre-screening and screening workflows based on the risk score, the scheduled events, and the procedure results, so that clinical trial coordinators can quickly assess where a candidate is in the pre-screening or screening process and what steps should be performed to move the patient forward in the process. The clinical trial coordinators can be presented with a prioritized list of clinical trial candidates based on any determined risk of having a disease and the current workflow state, so that the coordinators can efficiently focus their attention on screening the highest risk patients.

Figure 1:
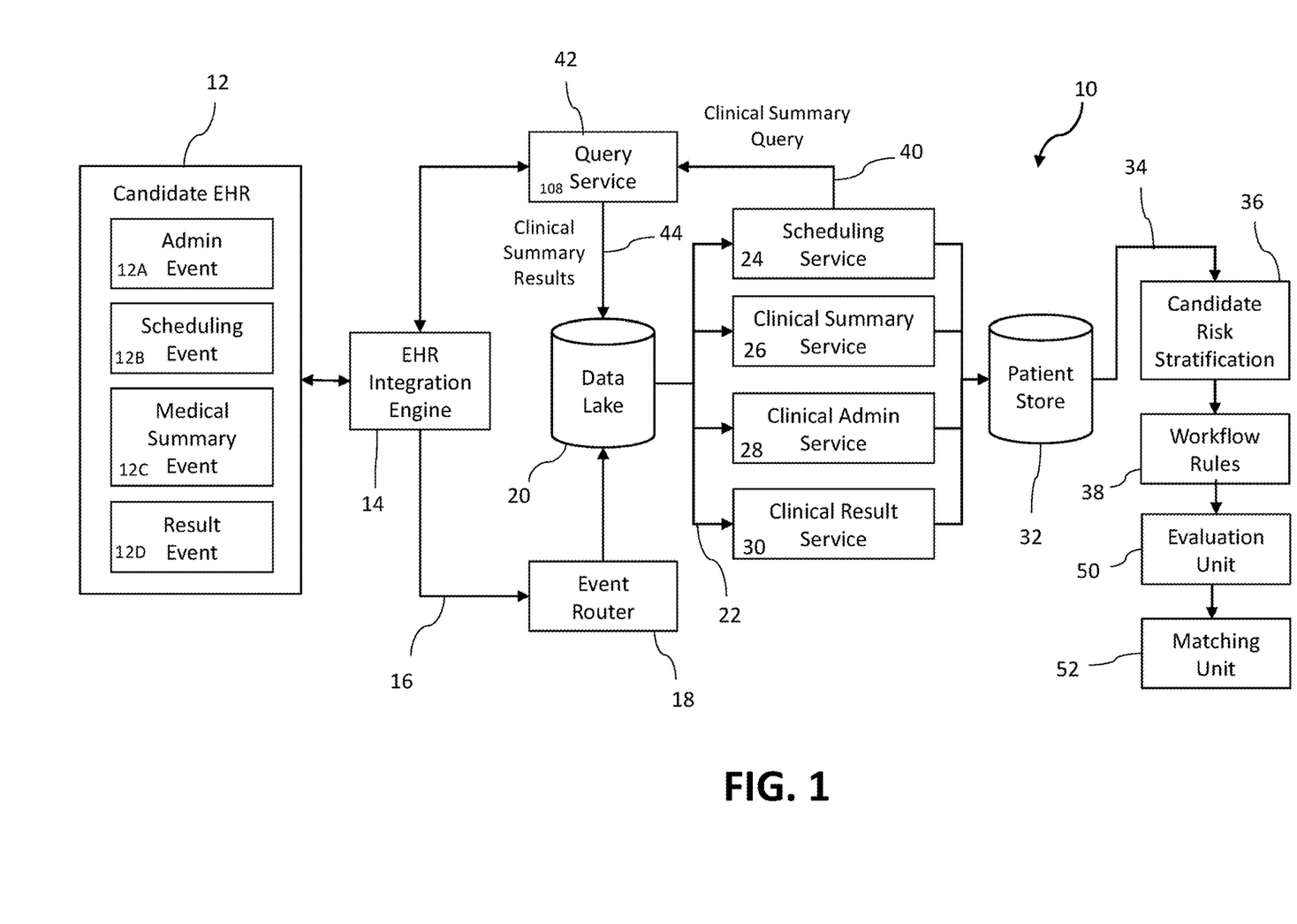
FIG. 1 is a schematic block diagram of a candidate identification system for identifying one or more candidates suitable for a clinical trial according to the teachings of the present invention.

FIG. 1 is a schematic diagram illustrating a candidate identification system 10 for identifying candidates for clinical trials according to the teachings of the present invention. The illustrated system 10 receives health related data from one or more data sources, such as client electronic health records or electronic health record systems, and then processes the health related data to compile and replicate the candidates appointment schedule and medical history. The resultant information is then used to risk stratify the candidate and apply workflow rules thereto. The illustrated system 10 includes one or more health related data sources 12 for providing health related data of a patient candidate. The health related data can include for example medical information, biological information, biometric information, identification information, administrative information such as admittance and discharge information, schedule and appointment related information, medical issues and problems, medication data, test information and related test results, physiologic and molecular biomarker information, and the like, of a patient candidate. The health related event data of the candidate can be provided to the system as an electronic health record (EHR) from an EHR system associated with one or more candidates. The health related data can specifically include, for example, administrative event data 12A that can include for example admittance information, discharge information, and transfer information about the candidate. The health related information can also include schedule event data 12B such as new, modified, and canceled appointment data. The candidate EHR can further include medical or clinical event data 12C such as medical history information including demographics, medical issues or problems, medical and test result information, medication information, diagnostic information, physical and biological measurement information, family history information, and social history information, as well as medical result event data 12D that includes test results. Although only a single candidate EHR is shown, those of ordinary skill in the art will readily recognize that multiple candidate EHRs from multiple EHR systems can be provided to the system 10.

The health related event data from the one or more data sources 12 is received by a data integration engine 14 that is configured for aggregating and integrating the various types of health related event data in the EHRs. Further, the data integration engine 14 parses and transforms or normalizes the event type data from the EHR into a standardized or normalized data format and forwards the normalized health related data 16 to an event router 18. The event router 18 generates a copy of the normalized health related data 16 for subsequent storage in a data storage element 20, such as a data lake. The data storage element 20 can be any selected type of data storage unit. The data lake 20 can be configured to store and replicate the normalized health related data 16 to form replicated health related data. The replicated normalized health related data 22 can be forwarded by the data lake 20 to an appropriate downstream service. Alternatively, the data lake can pass the original normalized data stored therein to the downstream data services. According to one embodiment, the replicated health data 22 can be conveyed to a scheduling service module 24 for processing any scheduling event data 12B present within the replicated health related data 22, and for updating the scheduling event data for subsequent storage in a patient candidate data storage unit 32. Further, the replicated health related data 22 can be conveyed to a clinical summary service module 26 for processing any clinical summary event data 12C from the EHR, such as the candidate's medical history, and for updating the patient's record in the patient data storage unit 32. Also, the replicated health related data 22 can be conveyed to a clinical administration event module 28 for processing any administration event data 12A and for updating the patient's record in the patient data storage unit 32. Still further, the replicated health related data 22 can be conveyed to a clinical result service module 30 for processing any test result data 12D present within the replicated health data and for updating the patient's record in the patient data storage unit 32.

The health related information 34 stored in the patient candidate data storage unit 32 can be conveyed to a candidate risk stratification unit 36 for applying thereto one or more risk stratification models or techniques. The risk stratification models can include, for example, one or more of clinical judgement, threshold, or predictive type models. According to one practice, the risk stratification model includes one or more predictive risk models for predicting or determining, based on the patient candidate data, which includes the health related data, whether the candidate is at risk of an unplanned hospital admission or for systematically categorizing candidates based on their health status. The predictive risk model can also be employed to assign risk levels having an associated risk score to the candidates. The predictive risk model is a statistical technique that can use one or more machine learning techniques to predict and forecast likely future outcomes based on historical and existing health related data, as well as based on trained risk models. Examples of suitable predictive risk models include classification models, clustering models, forecasting models, outlier models, or time series models, The predictive risk models can employ one or more predictive algorithms that can include, for example, artificial neural networks, random forest, generalized linear model, gradient boosted classifier model, K-means, or prophet type models. According to a preferred embodiment of the present invention, the candidate risk stratification unit 36 employs a gradient boosted classifier model to generate risk scores associated with each candidate, and then ranks the candidates based on the resultant risk scores. The candidate risk score can be used to determine whether the candidate is at-risk for one or more health conditions. As used herein, the term "condition" or "medical condition" or "health condition" is intended to mean a health impairment or condition of the body caused by an illness, disease, injury, lesion, or disorder, or an indication of a mental or physical state, of the candidate. The list of candidates and assigned risk scores generated by the candidate risk stratification unit 36 can be conveyed to a workflow rules unit 38 for computing and updating the workflow state of the candidate based on the updated clinical summary or patient candidate record (e.g., medical record) and risk scores according to a set of predetermined or preselected workflow rules. The patient candidate data can then be updated in the patient candidate data storage unit 32 so that the data can be queried or filtered by a user for display in a one or more selected user interfaces. The user interfaces can be generated by a user interface generator (not shown) associated with the system.

While multiple different types of event type data 12A-12D can be associated with the health related data 12 of the candidate, the clinical summary event data 12C can be further configured to request updates from the candidate EHR (health related data source 12) on demand. This feature is useful for situations where the system 10 has information about an upcoming appointment for the candidate and there is a need to risk stratify the candidate using the most up-to-date information in the candidate EHR before the appointment occurs. The determination as to whether to perform a system query is made by any selected portion of the system, such as by the scheduling service module 24, using the candidate's appointment information and status. If the query request is to be performed, a clinical summary query request 40 is generated by the scheduling service module 24 and is conveyed to a query service unit 42. The query service unit 42 then requests updated clinical summary event data 12C (e.g., medical history information) from the candidate EHR data integration engine 14. The data integration engine 14 transforms and forwards the data request from the query service unit 42 to the candidate EHR and sends the response with updated clinical summary event data 12C to the query service unit 42. The query service unit 42 then stores the results 44 of the updated clinical summary event data in the data lake 20, which then forwards the updated clinical summary event data to the clinical summary service module 26, which uses the updated health data to update the candidate's record in the patient candidate data storage unit 32, as well as update the risk score and workflow state via the candidate risk stratification unit 36 and the workflow rules unit 38. The query service unit 42 thus transmits any clinical summary queries to the candidate EHR 12 and stores the clinical summary results 44 in the data lake 20.

The candidate risk stratification unit 36 can employ the original and updated information to risk stratify the candidates by assigning risk scores related to a selected condition to each candidate and then ranking the candidates based on the risk scores. According to one embodiment, the candidates with risk scores above a risk score threshold level can be conveyed to the workflow rules unit 38 for further processing. The information associated with the ranked and scored candidates (e.g., risk score data) is then conveyed to the workflow rules unit 38 for applying one or more workflow rules thereto. The workflow rules are a finite state machine (identified in FIG. 3) that are designed to determine the correct state of the candidate in the recruitment, evaluation, intervention, and screening portions of the workflow process. At the present stage in the process, where we have just received a patient record update from the EHR, the finite state machine can automatically determine, using the candidate risk score, of whether or not the candidate should be recruited and evaluated for further research. The workflow rules determine the relative workflow position of the candidate within the candidate workflow. The workflow rules can include, for example, an assessment of the risk score of the candidate, a determination of whether an evaluation has been scheduled and performed, a determination of whether an intervention is required, a determination of whether the candidate meets the criteria of a clinical trial, a determination of whether a screening visit is required, and if so, whether it has been scheduled and then completed, and the like. Those of ordinary skill in the art will readily recognize that any selected number and type of workflow rules can be employed by the workflow rules unit 38 based on the type of information required, the specifics of the workflow of the system, and the like. The workflow rules unit 38 can then generate information associated with the position, status or workflow state within the workflow process for subsequent use by the system. Specifically, the workflow rules unit 38 conveys information associated with the appropriate workflow state of the candidate to the evaluation unit 50 based on the previous workflow state and any new information that was received in the updates to the health related data of the candidate.

The workflow state information can be received and processed by an evaluation unit 50 for evaluating the candidate, based on the workflow data, to gather further medical information from and about the candidate. The evaluation can be performed by the evaluation unit 50 via a series of user interface screens, where candidate health related data can be entered into the system. Alternatively, the evaluation unit 50 can receive health related data of the candidate by one more subject matter experts, such as a health professional, that meets or visits with the candidate to perform an examination of the candidate. The evaluation data generated by the evaluation unit 50 can be provided to a matching unit 52 for matching the candidate to one or more clinical trials. The clinical trials can be performed at a single site or at multiple different sites. The matching unit 52 can have prestored therein or can receive from a third party data source clinical summary data of the candidates that have been selected for various clinical trials. The clinical summary data can include relevant medical history information, which includes demographic information, medical issues or problem information, diagnostic information, medical and test result information, medication information, physical and biological measurement information, family history information, social history information, and the like.

Once the candidates are risk stratified, the workflow position of the candidate has been determined, and an evaluation is completed, the candidate is then matched with one or more clinical trials via the matching unit 52 based on the risk score data and the evaluation data. The matching unit 52 can employ one or more types of matching machine learning techniques, such as collaborative filtering, content-based filtering, similarity search, nearest-neighbors search, matrix factorization, or a tensor factorization technique, to generate a similarity score for each candidate. The tensor factorization technique decomposes a tensor into factor matrices that compactly store information encoded in a tensor and integrate interaction across different modes. The matrices include information associated with common factors between the candidates and participants (e.g., participants in a clinical trial) and a distance function is employed to derive a series of values. The common factors can include, for example, demographic information, problem and diagnosis history, body and biological measurement and vital history information, lab and test result history information, medical procedure history, medication history, social history, evaluation results from exams, visits, procedures, or other encounters performed in the evaluation unit 50, and time between selected events (e.g., diagnoses, results, procedures, medications, and the like). The values can be averaged to determine the similarity score. The similarity score is indicative of how similar the candidate is to a set of candidates or participants that have been approved for a specific clinical trial. The similarity score for each candidate is generated for each clinical trial. The matching unit thus operates as a recommender unit or system. The matching unit 52 can then rank or prioritize the similarity scores for all of the candidates at this stage. The matching unit thus generates similarity scores for all clinical trials and prioritizes the candidates for those trials by sorting the similarity scores in descending order such that the highest scoring clinical trial (i.e. the clinical trial for which the candidate is most similar to other candidates that enrolled) is at the top of the list. Those of ordinary skill in the art will readily recognize that the similarity scores can be sorted and presented in various ways. Thus, the matching unit 50 determines a candidate's likelihood of being approved to enter or participate in a selected clinical trial by comparing the medical history and evaluation results of the candidate with other participants that have successfully enrolled in each clinical trial. Further, the system or a system user can evaluate the medical history information of the candidate and compare the information with criteria, such as inclusion/exclusion criteria, of the clinical trial.

Figure 2:
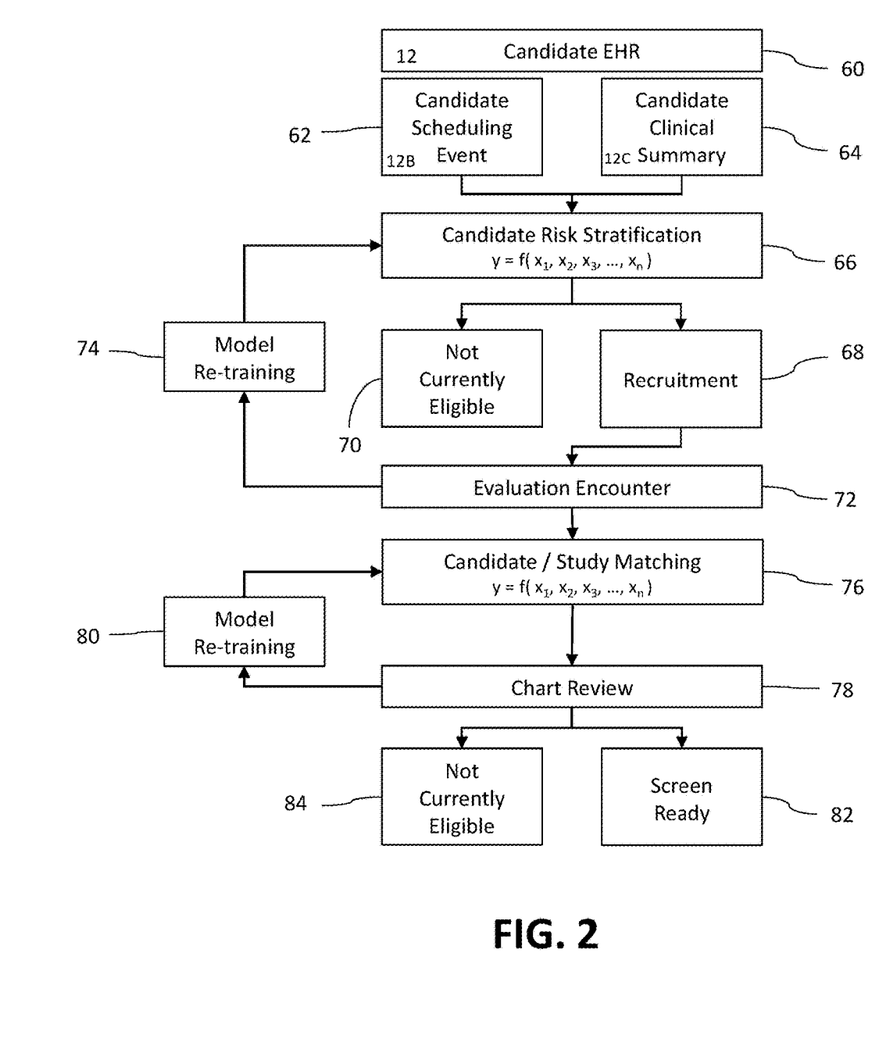
FIG. 2 is a schematic flow chart diagram illustrating a process by which candidates are identified as likely candidates for a clinical trial

FIG. 2 is a schematic flow chart diagram illustrating a process by which candidates are identified as likely candidates for a clinical trial by employing one or more risk stratification techniques, matching the health related data of the candidate to one or more studies or clinical trials, and applying one or more workflow rules. The health related data associated with the candidate is stored in the candidate EHR 12, step 60, and based on the data contained therein, the patient candidate data storage unit 32 can be populated or updated to include administration event data 12A, scheduling event data 12B, clinical summary event data 12C and result event data 12D. Specifically, the schedule event data 12B can include new, modified, and canceled appointment information, step 62. The candidate clinical summary event data 12C can include information that is representative of the candidate's medical history, including demographics, conditions or diseases, illnesses, test and diagnosis results, medications, measurements, family history, social history, and the like, step 64.

The candidate can then be risk stratified by the candidate risk stratification unit 36, step 66. In this regard, the candidate risk stratification unit 36 can apply a predictive risk model, such as a gradient boosted classifier model, to the health related data to generate a risk score associated with one or more conditions or diseases for each candidate. The predictive risk model can be tailored or trained to one or more specific conditions. To that end, the candidate risk stratification unit 36 determines a risk score for each candidate based on each selected condition. The candidates can then be ranked or stratified based on the risk scores associated with each condition. The candidate risk stratification unit 36 thus employs the predictive risk model for computing a risk score that represents a patient's risk for a specific condition or propensity for suffering symptom or complications associated with the specific condition. The model can be fully trained based on one or more specific conditions and associated symptoms. The candidates that have higher risk scores or scores higher than a selected threshold risk score can be classified as recruitable and prioritized for subsequent evaluation for suitability to join a clinical trial, step 68. Conversely, candidates that have lower risk scores or scores lower than a selected threshold risk score can be classified as not eligible for a selected clinical trial, step 70. According to one embodiment, the threshold risk score can be about 60%. The recruitment and lack of eligibility steps can be characterized as work flow states. As used herein, the term "clinical trial" is intended to include health or medical related studies, research or trials that are directed to discovering or learning more about human health or a selected condition or how a proposed treatment can affect the condition or the health of the human. The trials can include a scientifically controlled study of the safety and effectiveness of a therapeutic agent using consenting human candidates. The candidates that are suitable for recruitment (e.g., recruitment state in the workflow process) are evaluated for further screening via an evaluation encounter that occurs either virtually or in a health care setting, such as in a clinic, step 72. During the evaluation encounter, the candidate can be further evaluated and additional health related data can be generated and entered via the evaluation unit 50. Alternatively, the system user can enter health related information involving the candidate directly into the system. The datasets of the predictive risk model employed by the candidate risk stratification unit 36 can be further enhanced and trained using the outputs of the predictive risk model, step 74. The risk stratification models can be trained on populations of candidates that have been ingested from the EHR in the past for which there is a confirmed diagnosis for a given condition, confirmed complications for a given condition, or documentation to rule-out a given condition. The models can be trained on the same clinical summary data described herein (e.g., demographics, problems, diagnoses, results, procedures, medications, notes, etc.).

Once the candidates are risk stratified, sorted (e.g., recruited), and evaluated, the candidates with the highest ranked risk scores are then matched with one or more clinical trials, step 76. Specifically, the matching unit 52 employs one or more matching models to determine a candidate's likelihood of enrolling in a clinical trial by comparing the candidate's medical history and evaluation results with other candidates or participants who have successfully enrolled or participated in the clinical trial. Specifically, the matching unit 52 can generate a similarity score for each recruited candidate based on their medical history, the risk scores and the evaluation data. The similarity scores are then ranked or prioritized. The similarity score is indicative of how similar the candidate is to participants in each clinical trial. The matching unit 52 can generate similarity scores for each candidate for each clinical trial that the system is being employed to match. The matching models are trained on populations of patients that have successfully screened or enrolled in active clinical trials. The models are trained on the same clinical summary data described herein (e.g., demographics, problems, diagnoses, results, procedures, medications, notes, etc.), as well as data that has been generated by earlier steps in the process, such as risk scores and evaluation encounter results. The matched candidates are then identified and then scheduled to meet with one or more health professionals for further evaluation (e.g., chart review), step 78. The chart review step enables the system to identify the candidates best suited for the clinical trial. The candidates who meet the criteria for the clinical trial are identified are placed into a screen ready work flow state, step 82, while the candidates that do not meet the criteria of the clinical trial are moved into a not currently eligible workflow state, step 84. The candidates that do not meet the criteria can be re-evaluated for eligibility at a later time. The model employed by the matching unit 52 can be trained using the proper training data, and can be further enhanced and trained using the candidates identified by the matching unit, step 80.

Figure 3:
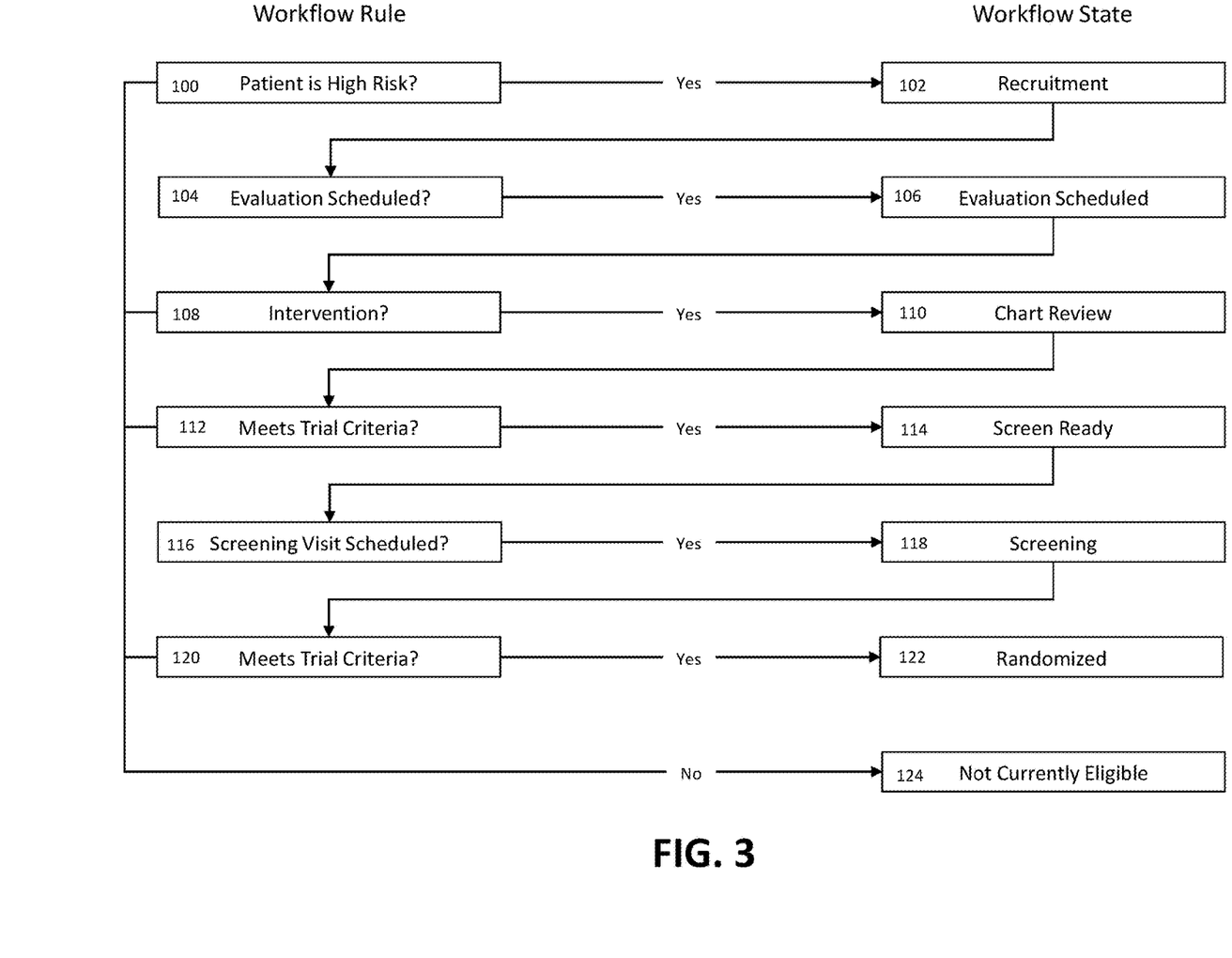
FIG. 3 is a schematic flow chart diagram of the workflow rules applied by the workflow rules unit of the candidate identification system of the present invention.

FIG. 3 is a schematic flow chart diagram of the workflow rules applied by the workflow rules unit 38 of the candidate identification system 10 of the present invention. The workflow rules applied by the workflow rules unit 38 of the system determine the workflow state of a selected candidate. The workflow rules determine which step in the recruitment, evaluation, and screening process the candidate should preside in based on a previous step and any new health related information that has been received. For example, the patient candidate risk stratification unit 36 calculates or determines a risk score associated with each candidate based on the health data 12 and generates risk score data. The risk score data is processed by the workflow rules unit 38 and applies one or more workflow rules thereto. The workflow rules are compared to the candidate's medical history, such as the candidate's including demographics, diagnoses, observations, family history, and social history, as well to clinical trial history and risk score. The workflow rules can include, for example, a determination of whether a candidate has a high risk score assigned thereto by the patient candidate risk stratification unit 36, step 100. That is, the candidate has a risk score above the risk score threshold level. If the candidate has a high risk score, then the system is placed in a workflow state that identifies the candidate as being suitable for the recruitment process, step 102. If the candidate does not have a high risk score, then the system is placed in a workflow state that identifies the candidate as not being currently eligible for any selected clinical trial, step 124. As illustrated, any answer to the negative of any of the work rules is indicative of the candidate as not being currently eligible for a clinical trial. When the workflow rule is satisfied, then the system applies additional workflow rules until the predetermined set of workflow rules is satisfied absent determinations to the negative. In the current example, the workflow rules unit 38 can then apply an evaluation scheduled rule once the candidate is identified as being recruitable for a clinical trial, step 104. The evaluation schedule related to the evaluation encounter of step 72, FIG. 2. The evaluation workflow rule determines whether a patient has received an abnormal result from the evaluation encounter (e.g., a visit, procedure, or questionnaire, conducted in-person or virtually). If an evaluation is scheduled, then the system is placed in a workflow state that identifies candidates that have a future appointment scheduled. The evaluation can be automatically scheduled, an alert can be sent requesting that the candidate schedule an evaluation, or prompt a system user to follow-up with the candidate to schedule an evaluation, step 106.

The workflow rules unit 38 can then apply an intervention workflow rule to determine if a candidate intervention is required, step 108. That is, the workflow rule determines whether the candidate has been evaluated. If so, then the system is placed in a chart review workflow state (FIG. 2, step 78) that identifies candidates who are at high-risk for a disease, as determined by the patient candidate risk stratification unit 36 and evaluation encounter, and are ready to have their medical history evaluated and compared with the candidates that have qualified for one or more clinical trials, such as by the matching unit 52. The matching unit 52 prioritizes the candidates for chart review, step 110. The candidates are chart reviewed for best matching with the clinical trials. The workflow rules unit 38 can than apply a meets trial criteria workflow rule that identifies whether the candidate meets the criteria of the clinical trial, step 112. If so, then the system is placed in a screen ready workflow state that identifies the candidates that are eligible and ready to screen for a particular clinical trial, step 114.

Further, the workflow rules unit 38 applies a screening visit scheduled workflow rule to the risk score data that identifies the candidates that have a future screening visit appointment scheduled, step 116. If the appointment is scheduled, then the system is placed in a screening workflow state that identifies the candidates that are currently in the screening process for a selected clinical trial, step 118. Still further, the workflow rules unit 38 applies a meets trial criteria workflow rule that identifies whether a candidate meets the screening criteria for the clinical trial, step 120. If so, then the system is placed in a workflow state that identifies the candidates who have successfully been randomized for a particular clinical trial, step 122. Those of ordinary skill in the art will readily recognize that different types of rules can be applied by the workflow rules unit 38 as a function of the health related data 12 and the requirements or criteria of the clinical trial.

Figure 4A:
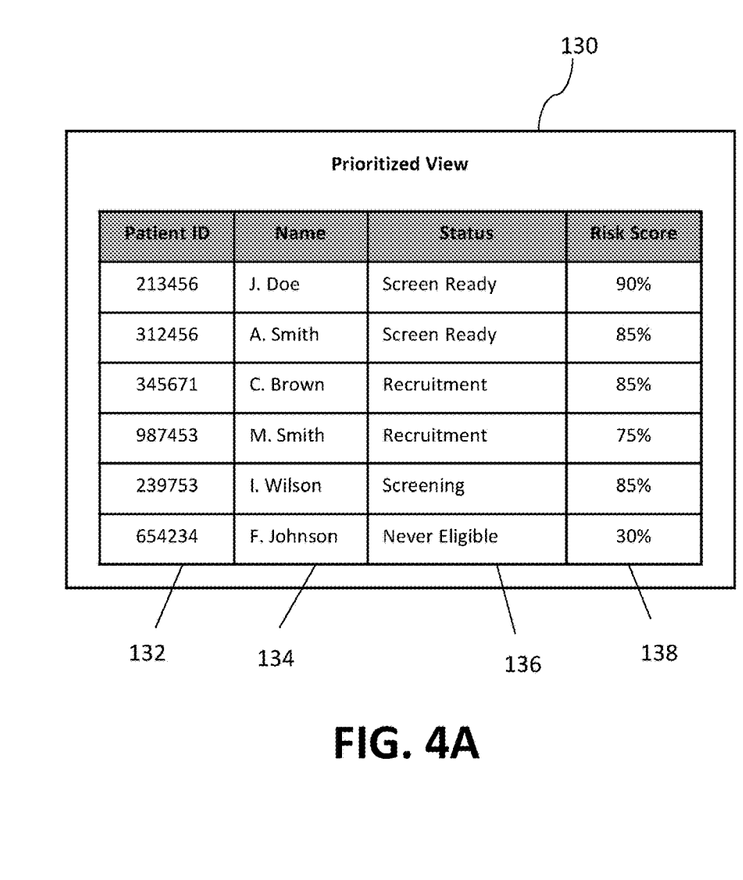
FIG. 4A is a schematic representation of data in a table format that is prioritized based on one or more of risk score and workflow status.
Figure 4B:
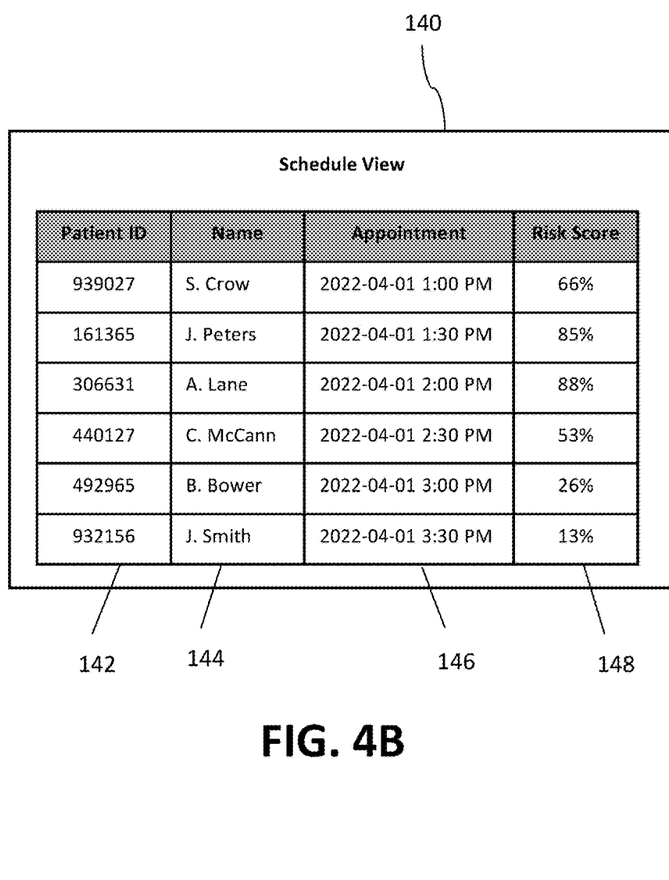
FIG. 4B is a schematic representation of data in a table format that is prioritized based on schedule data.

The candidate identification system 10 of the present invention can also rank or prioritize the candidates based on risk score, scheduled appointments, or other data types, as shown for example in FIGS. 2, 4A and 4B. The risk score data, schedule appointment data, candidate data, and the like can be stored in the patient candidate data storage unit 32. The data can be stored in any selected data format and can be stored and retrieved as structured data, such as in a table format. FIG. 4A shows a table 130 that sets forth candidate specific information generated by the present invention. For example, the table 130 includes columns 132, 134 that include candidate related data, including identification information. The illustrated table 130 can also include a column 136 that sets forth the workflow status of the candidate, such as screen ready workflow state, recruitment workflow state, not currently eligible workflow state, and the like. The table 130 also includes a column 138 that sets forth the risk scores assigned to each of the candidates in the table. The information in the table 130 is stratified or prioritized based on the workflow status and the risk score, starting with the highest assigned risk scores and the prioritized workflow status. The workflow state has priority over the risk score such that the candidates that are further along in the workflow process are ranked higher than those that are earlier in the workflow process. For example, a candidate in chart review with a high risk score would take precedence or have priority over a candidate in an earlier stage of the workflow process with a high risk score. The candidates in the table 130 that have risk scores above a risk score threshold level, such as a risk score of at least about 60%, would be eligible for recruitment. As such, in the current example, the candidate (F. Johnson) with the risk score of 30% is less than the threshold, and hence is not currently eligible for recruitment. Further, the candidates that are further along the workflow process (FIG. 3) are prioritized over candidates earlier in the workflow process. The status priority (e.g., workflow state) can be, for example, from highest priority to lowest priority, screen ready, recruitment, and screening.

Similarly, as shown in FIG. 4B, the illustrated table 40 sets forth candidate information that is stratified or prioritized based on scheduling information. Specifically, the table 140 includes columns 142, 144 that sets forth candidate related data, including identification information. The illustrated table 140 can also include a column 146 that sets forth the appointment or scheduling information of the candidate, including the date and time of the appointment. The table 140 can also include a column 148 that sets forth the risk scores assigned to each of the candidates in the table by the candidate risk stratification unit 36. The information in the table 140 is stratified, ranked or prioritized based on the schedule date and time.

Figure 5:
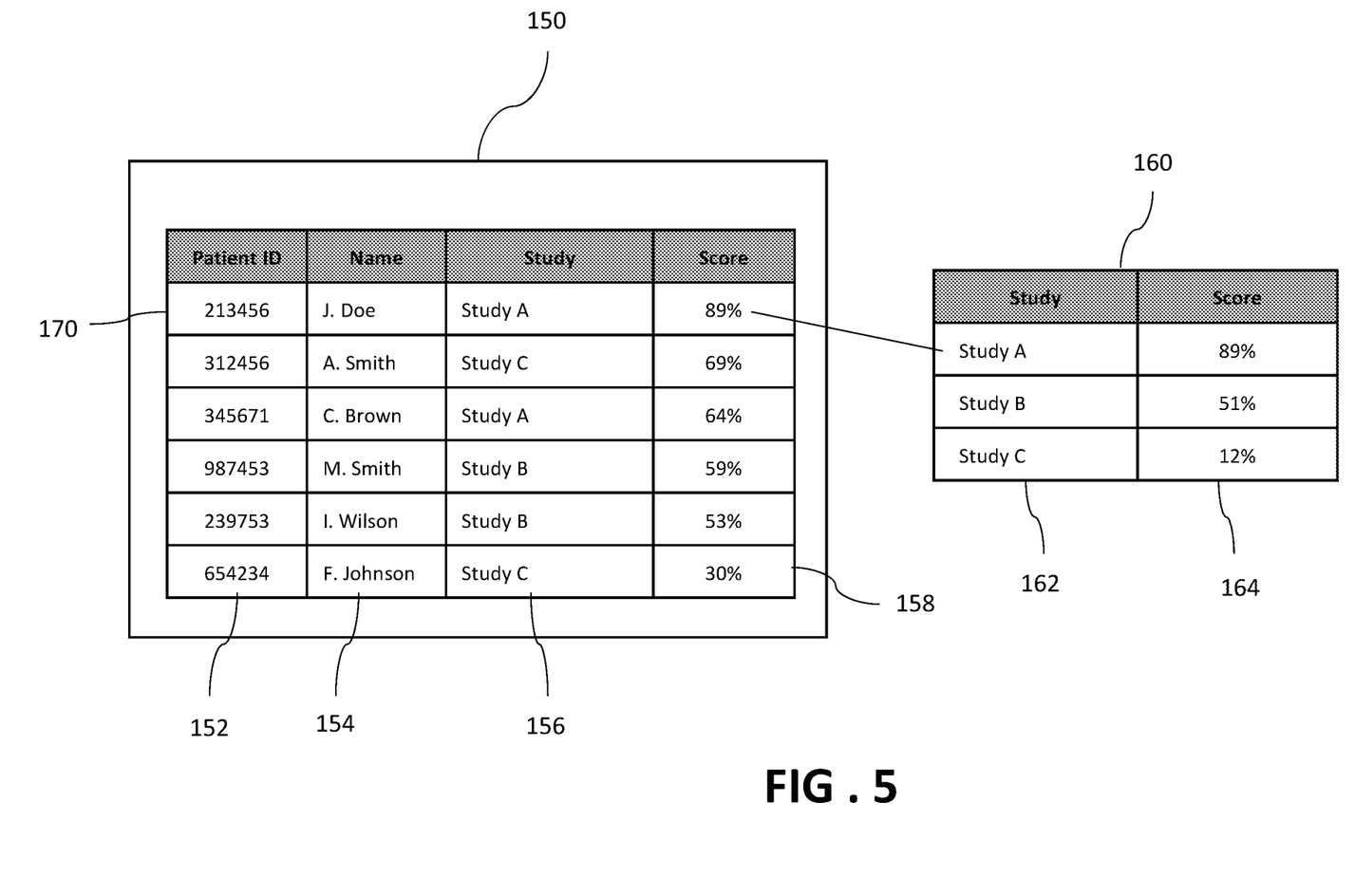
FIG. 5 is a schematic representation of data in a table format that is prioritized or ranked based on similarity scores.

FIG. 5 shows a table stored in the patient candidate storage unit 32, for example, that includes a list of candidates that are ranked according to the similarity scores generated by the matching unit 52. For example, the table 150 includes columns 152, 154 that sets forth candidate related data, including identification information. The illustrated table 150 can also include a column 156 that sets forth information identifying a selected clinical trial, such as, in the current example, Study A, Study B, and Study C. The table 150 can also include a column 158 that sets forth the similarity scores assigned to each of the candidates in the table by the matching unit 52. The similarity scores are indicative of the similarity between the candidate and the participants in the clinical trial. The information in the table 150 can be stratified, ranked or prioritized based on the similarity scores.

The illustrated table 160 sets forth clinical trial information associated with the identified candidate 170 from table 150. The table 160 lists in column 162 the clinical trials that the system has attempted to match the identified candidate 170, along with the similarity scores for each of the clinical trials, as shown in column 164. The similarity scores of the candidates are ranked by the matching unit according to the best match or highest scoring clinical trial. For example, Study A takes precedence for candidate J. Doe because it has the highest score. However, if Study A were ruled out for the candidate J. Doe (e.g., lack of interest, ineligibility based on missing information, or screen failure, and the like), then the candidate J. Doe can be placed in the "Not Currently Eligible" state of Study A and then Study B takes precedence for the Chart Review.

It is to be understood that although the invention has been described above in terms of particular embodiments, the foregoing embodiments are provided as illustrative only, and do not limit or define the scope of the invention. Various other embodiments, including but not limited to those described herein are also within the scope of the claims. For example, elements, units, tools and components described herein may be further divided into additional components or joined together to form fewer components for performing the same functions. Any of the functions disclosed herein may be implemented using means for performing those functions. Such means include, but are not limited to, any of the components disclosed herein, such as the electronic or computing device components described herein.

The techniques described above may be implemented, for example, in hardware, one or more computer programs tangibly stored on one or more computer-readable media, firmware, or any combination thereof. The techniques described above may be implemented in one or more computer programs executing on (or executable by) a programmable computer including any combination of any number of the following: a processor, a storage medium readable and/or writable by the processor (including, for example, volatile and non-volatile memory and/or storage elements), an input device, and an output device. Program code may be applied to input entered using the input device to perform the functions described and to generate output using the output device.

The term computing device or electronic device can refer to any device that includes a processor and a computer-readable memory capable of storing computer-readable instructions, and in which the processor is capable of executing the computer-readable instructions in the memory. The terms computer system and computing system refer herein to a system containing one or more computing devices.

Embodiments of the present invention include features which are only possible and/or feasible to implement with the use of one or more computers, computer processors, and/or other elements of a computer system. Such features are either impossible or impractical to implement mentally and/or manually. For example, embodiments of the present invention may operate on digital electronic processes which can only be created, stored, modified, processed, and transmitted by computing devices and other electronic devices. Such embodiments, therefore, address problems which are inherently computer-related and solve such problems using computer technology in ways which could not be solved manually or mentally by humans.

Any claims herein which affirmatively require a computer, a processor, a memory, or similar computer-related elements, are intended to require such elements, and should not be interpreted as if such elements are not present in or required by such claims. Such claims are not intended, and should not be interpreted, to cover methods and/or systems which lack the recited computer-related elements. For example, any method claim herein which recites that the claimed method is performed by a computer, a processor, a memory, and/or similar computer-related element, is intended to, and should only be interpreted to, encompass methods which are performed by the recited computer-related element(s). Such a method claim should not be interpreted, for example, to encompass a method that is performed mentally or by hand (e.g., using pencil and paper). Similarly, any product claim herein which recites that the claimed product includes a computer, a processor, a memory, and/or similar computer-related element, is intended to, and should only be interpreted to, encompass products which include the recited computer-related element(s). Such a product claim should not be interpreted, for example, to encompass a product that does not include the recited computer-related element(s).

Embodiments of the present invention solve one or more problems that are inherently rooted in computer technology. For example, embodiments of the present invention solve the problem of how to associate a technical artifact with a node of a process flow diagram. There is no analog to this problem in the non-computer environment, nor is there an analog to the solutions disclosed herein in the non-computer environment. Embodiments can also associate steps or nodes on a business process with business rules, showing an operator which rules are exercised by a step or node in the process, or conversely, which steps or nodes refer to a particular business rule.

Furthermore, embodiments of the present invention represent improvements to computer and communication technology itself. For example, the system 10 of the present can optionally employ a specially programmed or special purpose computer in an improved computer system, which may, for example, be implemented within a single computing device.

Each computer program within the scope of the claims below may be implemented in any programming language, such as assembly language, machine language, a high-level procedural programming language, or an object-oriented programming language. The programming language may, for example, be a compiled or interpreted programming language.

Each such computer program or system module or unit may be implemented in a computer program product tangibly embodied in a machine-readable storage device for execution by a computer processor. Method steps of the invention may be performed by one or more computer processors executing a program tangibly embodied on a computer-readable medium to perform functions of the invention by operating on input and generating output. Suitable processors include, by way of example, both general and special purpose microprocessors. Generally, the processor receives (reads) instructions and data from a memory (such as a read-only memory and/or a random access memory) and writes (stores) instructions and data to the memory. Storage devices suitable for tangibly embodying computer program instructions and data include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive (read) programs and data from, and write (store) programs and data to, a non-transitory computer-readable storage medium such as an internal disk (not shown) or a removable disk. These elements can also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

Any data disclosed herein may be implemented, for example, in one or more data structures tangibly stored on a non-transitory computer-readable medium. Embodiments of the invention may store such data in such data structure(s) and read such data from such data structure(s).

It should be appreciated that various concepts, systems and methods described above can be implemented in any number of ways, as the disclosed concepts are not limited to any particular manner of implementation or system configuration. Examples of specific implementations and applications are discussed below and shown in FIG. 6 primarily for illustrative purposes and for providing or describing the operating environment of the system of the present invention. The candidate identification system 10 and/or any elements, components, or units thereof can employ one or more electronic or computing devices, such as one or more servers, clients, computers, laptops, smartphones and the like, that are networked together or which are arranged so as to effectively communicate with each other. The network can be any type or form of network. The devices can be on the same network or on different networks. In some embodiments, the network system may include multiple, logically-grouped servers. In one of these embodiments, the logical group of servers may be referred to as a server farm or a machine farm. In another of these embodiments, the servers may be geographically dispersed. The electronic devices can communicate through wired connections or through wireless connections. The clients can also be generally referred to as local machines, clients, client nodes, client machines, client computers, client devices, endpoints, or endpoint nodes. The servers can also be referred to herein as servers, server nodes, or remote machines. In some embodiments, a client has the capacity to function as both a client or client node seeking access to resources provided by a server or server node and as a server providing access to hosted resources for other clients. The clients can be any suitable electronic or computing device, including for example, a computer, a server, a smartphone, a smart electronic pad, a portable computer, and the like, such as the electronic or computing device 400. The present invention can employ one or more of the illustrated computing devices and can form a computing system. Further, the server may be a file server, application server, web server, proxy server, appliance, network appliance, gateway, gateway server, virtualization server, deployment server, SSL VPN server, or firewall, or any other suitable electronic or computing device, such as the electronic device 400. In one embodiment, the server may be referred to as a remote machine or a node. In another embodiment, a plurality of nodes may be in the path between any two communicating servers or clients. The process flow identification system 10 which includes the data extraction unit 14, the storage unit 18, the rule identification unit 34, the project explorer tool 24, the process flow diagram unit 26, the visual application unit 28, and the architecture diagram unit 30 can be stored on one or more of the clients or servers, and the hardware associated with the client or server, such as the processor or CPU and memory described below.

Figure 6:
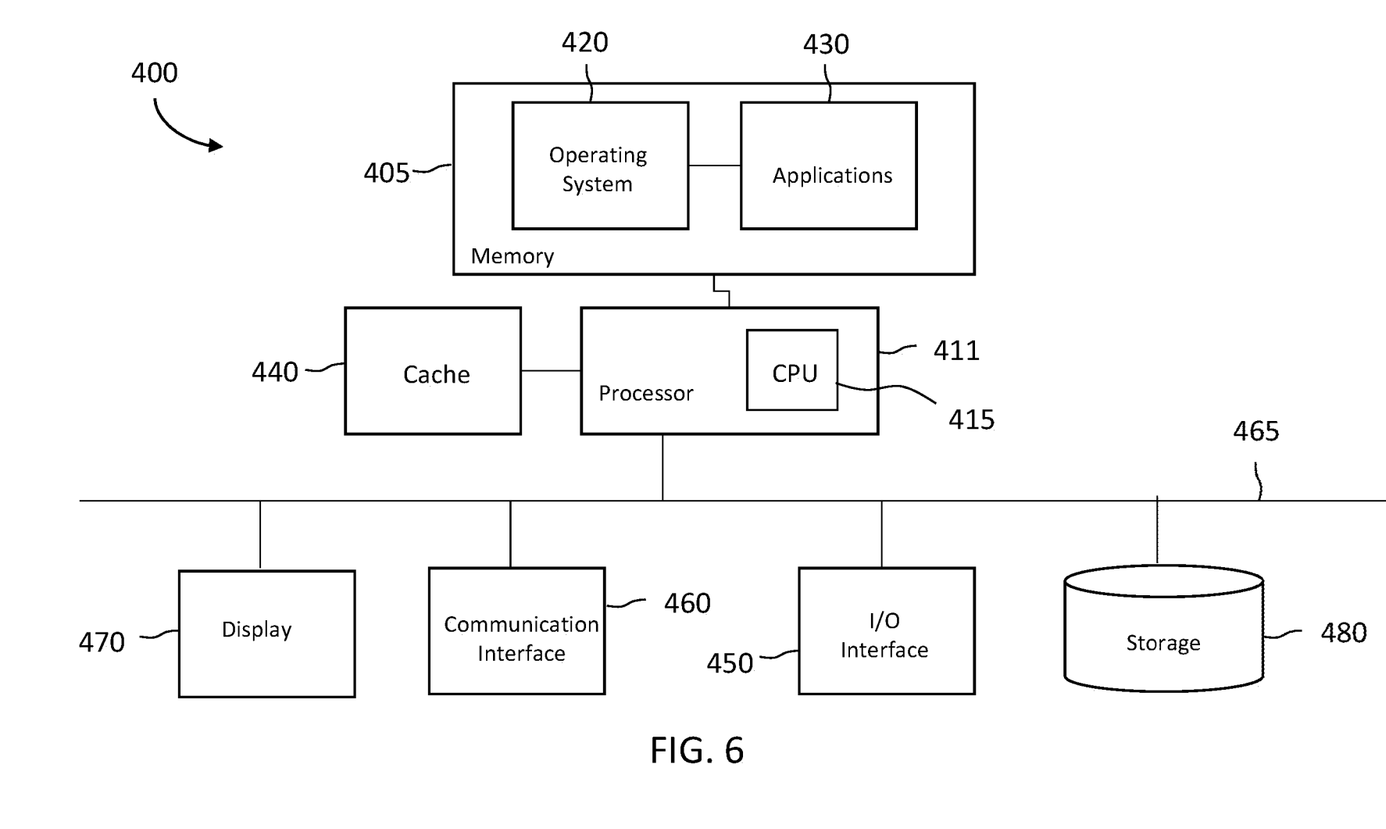
FIG. 6 is a schematic diagram of an electronic device and/or associated system suitable for implementing the process flow identification system of the present invention.

FIG. 6 is a high-level block diagram of an electronic or computing device 400 that can be used with the embodiments disclosed herein. Without limitation, the hardware, software, and techniques described herein can be implemented in digital electronic circuitry or in computer hardware that executes firmware, software, or combinations thereof. The implementation can include a computer program product (e.g., a non-transitory computer program tangibly embodied in a machine-readable storage device, for execution by, or to control the operation of, one or more data processing apparatuses, such as a programmable processor, one or more computers, one or more servers and the like).

The illustrated electronic device 400 can be any suitable electronic circuitry that includes a main memory unit 405 that is connected to a processor 411 having a CPU 415 and a cache unit 440 configured to store copies of the data from the most frequently used main memory 405. The electronic device can implement the process flow identification system 10 or one or more elements of the process flow identification system.

Further, the methods and procedures for carrying out the methods disclosed herein can be performed by one or more programmable processors executing a computer program to perform functions of the invention by operating on input data and generating output. Further, the methods and procedures disclosed herein can also be performed by, and the apparatus disclosed herein can be implemented as, special purpose logic circuitry, such as a FPGA (field programmable gate array) or an ASIC (application specific integrated circuit). Modules and units disclosed herein can also refer to portions of the computer program and/or the processor/special circuitry that implements that functionality.

The processor 411 is any logic circuitry that responds to, processes or manipulates instructions received from the main memory unit, and can be any suitable processor for execution of a computer program. For example, the processor 411 can be a general and/or special purpose microprocessor and/or a processor of a digital computer. The CPU 415 can be any suitable processing unit known in the art. For example, the CPU 415 can be a general and/or special purpose microprocessor, such as an application-specific instruction set processor, graphics processing unit, physics processing unit, digital signal processor, image processor, coprocessor, floating-point processor, network processor, and/or any other suitable processor that can be used in a digital computing circuitry. Alternatively or additionally, the processor can comprise at least one of a multi-core processor and a front-end processor. Generally, the processor 411 can be embodied in any suitable manner. For example, the processor 411 can be embodied as various processing means such as a microprocessor or other processing element, a coprocessor, a controller or various other computing or processing devices including integrated circuits such as, for example, an ASIC (application specific integrated circuit), an FPGA (field programmable gate array), a hardware accelerator, or the like. Additionally or alternatively, the processor 411 can be configured to execute instructions stored in the memory 405 or otherwise accessible to the processor 411. As such, whether configured by hardware or software methods, or by a combination thereof, the processor 411 can represent an entity (e.g., physically embodied in circuitry) capable of performing operations according to embodiments disclosed herein while configured accordingly. Thus, for example, when the processor 411 is embodied as an ASIC, FPGA or the like, the processor 411 can be specifically configured hardware for conducting the operations described herein. Alternatively, as another example, when the processor 411 is embodied as an executor of software instructions, the instructions can specifically configure the processor 411 to perform the operations described herein. In many embodiments, the central processing unit 530 is provided by a microprocessor unit, e.g.: those manufactured by Intel Corporation of Mountain View, Calif.; those manufactured by Motorola Corporation of Schaumburg, Ill.; the ARM processor and TEGRA system on a chip (SoC) manufactured by Nvidia of Santa Clara, Calif.; the POWER7 processor, those manufactured by International Business Machines of White Plains, N.Y.; or those manufactured by Advanced Micro Devices of Sunnyvale, Calif. The processor can be configured to receive and execute instructions received from the main memory 405.

The electronic device 400 applicable to the hardware of the present invention can be based on any of these processors, or any other processor capable of operating as described herein. The central processing unit 415 may utilize instruction level parallelism, thread level parallelism, different levels of cache, and multi-core processors. A multi-core processor may include two or more processing units on a single computing component. Examples of multi-core processors include the AMD PHENOM IIX2, INTEL CORE i5 and INTEL CORE i7.

The processor 411 and the CPU 415 can be configured to receive instructions and data from the main memory 405 (e.g., a read-only memory or a random access memory or both) and execute the instructions The instructions and other data can be stored in the main memory 405. The processor 411 and the main memory 405 can be included in or supplemented by special purpose logic circuitry. The main memory unit 405 can include one or more memory chips capable of storing data and allowing any storage location to be directly accessed by the processor 411. The main memory unit 405 may be volatile and faster than other memory in the electronic device, or can dynamic random access memory (DRAM) or any variants, including static random access memory (SRAM), Burst SRAM or SynchBurst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM). In some embodiments, the main memory 405 may be non-volatile; e.g., non-volatile read access memory (NVRAM), flash memory non-volatile static RAM (nvSRAM), Ferroelectric RAM (FeRAM), Magnetoresistive RAM (MRAM), Phase-change memory (PRAM), conductive-bridging RAM (CBRAM), Silicon-Oxide-Nitride-Oxide-Silicon (SONOS), Resistive RAM (RRAM), Racetrack, Nano-RAM (NRAM), or Millipede memory. The main memory 405 can be based on any of the above described memory chips, or any other available memory chips capable of operating as described herein. In the embodiment shown in FIG. 6, the processor 411 communicates with main memory 405 via a system bus 465. The computer executable instructions of the present invention may be provided using any computer-readable media that is accessible by the computing or electronic device 400. Computer-readable media may include, for example, the computer memory or storage unit 405. The computer storage media may also include, but is not limited to, RAM, ROM, EPROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device. In contrast, communication media may embody computer readable instructions, data structures, program modules, or other data in a modulated data signal, such as a carrier wave, or other transport mechanism. As defined herein, computer readable storage media does not include communication media. Therefore, a computer storage or memory medium should not be interpreted to be a propagating signal per se or stated another transitory in nature. The propagated signals may be present in a computer storage media, but propagated signals per se are not examples of computer storage media, which is intended to be non-transitory. Although the computer memory or storage unit 405 is shown within the computing device 400 it will be appreciated that the storage may be distributed or located remotely and accessed via a network or other communication link.

The main memory 405 can comprise an operating system 420 that is configured to implement various operating system functions. For example, the operating system 420 can be responsible for controlling access to various devices, memory management, and/or implementing various functions of the asset management system disclosed herein. Generally, the operating system 420 can be any suitable system software that can manage computer hardware and software resources and provide common services for computer programs.

The main memory 405 can also hold application software 430. For example, the main memory 405 and application software 430 can include various computer executable instructions, application software, and data structures, such as computer executable instructions and data structures that implement various aspects of the embodiments described herein. For example, the main memory 405 and application software 430 can include computer executable instructions, application software, and data structures, such as computer executable instructions and data structures that implement various aspects of the content characterization systems disclosed herein, such as processing and capture of information. Generally, the functions performed by the content characterization systems disclosed herein can be implemented in digital electronic circuitry or in computer hardware that executes software, firmware, or combinations thereof. The implementation can be as a computer program product (e.g., a computer program tangibly embodied in a non-transitory machine-readable storage device) for execution by or to control the operation of a data processing apparatus (e.g., a computer, a programmable processor, or multiple computers). Generally, the program codes that can be used with the embodiments disclosed herein can be implemented and written in any form of programming language, including compiled or interpreted languages, and can be deployed in any form, including as a stand-alone program or as a component, module, subroutine, or other unit suitable for use in a computing environment. A computer program can be configured to be executed on a computer, or on multiple computers, at one site or distributed across multiple sites and interconnected by a communications network, such as the Internet.

The processor 411 can further be coupled to a database or data storage 480. The data storage 480 can be configured to store information and data relating to various functions and operations of the content characterization systems disclosed herein. For example, as detailed above, the data storage 480 can store information including but not limited to captured information, multimedia, processed information, and characterized content.

A wide variety of I/O devices may be present in or connected to the electronic device 400. For example, the electronic device can include a display 470, and as previously described, the visual application unit 28 or one or more other elements of the system 10 can include the display. The display 470 can be configured to display information and instructions received from the processor 411. Further, the display 470 can generally be any suitable display available in the art, for example a Liquid Crystal Display (LCD), a light emitting diode (LED) display, digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays, or electronic papers (e-ink) displays. Furthermore, the display 470 can be a smart and/or touch sensitive display that can receive instructions from a user and forwarded the received information to the processor 411. The input devices can also include user selection devices, such as keyboards, mice, trackpads, trackballs, touchpads, touch mice, multi-touch touchpads, touch mice and the like, as well as microphones, multi-array microphones, drawing tablets, cameras, single-lens reflex camera (SLR), digital SLR (DSLR), CMOS sensors, accelerometers, infrared optical sensors, pressure sensors, magnetometer sensors, angular rate sensors, depth sensors, proximity sensors, ambient light sensors, gyroscopic sensors, or other sensors. The output devices can also include video displays, graphical displays, speakers, headphones, inkjet printers, laser printers, and 3D printers.

The electronic device 400 can also include an Input/Output (I/O) interface 450 that is configured to connect the processor 411 to various interfaces via an input/output (I/O) device interface 480. The device 400 can also include a communications interface 460 that is responsible for providing the circuitry 400 with a connection to a communications network (e.g., communications network 120). Transmission and reception of data and instructions can occur over the communications network.

We claim:

1. A candidate identification system for identifying a plurality of candidates for one or more clinical trials, comprising
one or more data sources for providing health related data associated with each of the plurality of candidates,
an integration engine for integrating the health related data to form normalized health related data,
a data storage element for storing the normalized health related data,
a risk stratification unit for applying a predictive risk model to the normalized health related data and for generating and assigning a risk score to each of the plurality of candidates based on a selected condition and then ranking each of the plurality of candidates based on the risk score, wherein the risk stratification unit is configured to compare the assigned risk scores with a threshold risk score, and wherein the predictive risk model is configured to predict and forecast likely future outcomes based on one or more trained risk models and historical health related data, and wherein the predictive risk model comprises at least one of a neural network model, a random forest model, a generalized linear model, a gradient boosted classifier model, a K-means clustering model, or a time series forecasting model, and a matching unit for employing one or more matching machine learning techniques to generate a similarity score for each of the plurality of candidates having the assigned risk score higher than the threshold risk score, wherein the similarity score is indicative of a similarity between each of the plurality of candidates and one or more participants in the one or more clinical trials, wherein the one or more matching machine learning techniques includes a tensor factorization technique that decomposes a tensor into factor matrices storing information encoded in the tensor, wherein the similarity score is determined based on the information in the factor matrices, and wherein the similarity score is an average of values in the factor matrices.

2. The system of claim 1, further comprising a workflow rules unit for applying one or more workflow rules to each of the plurality of candidates, and an evaluation unit for providing evaluation data about each of the plurality of candidates.

3. The system of claim 2, wherein the matching unit matches each of the candidates to one or more clinical trials based on the evaluation data and based on the risk score data.

4. The system of claim 3, wherein the matching unit further matches each of the candidates to one or more clinical trials based on the health related data.

5. The system of claim 4, wherein the evaluation unit determines, based on the assigned risk scores of each of the candidates, which of the candidates are to be evaluated.

6. The system of claim 5, wherein the matching unit ranks the plurality of candidates based on the similarity scores of the plurality of candidates.

7. The system of claim 6, wherein the risk score generated by the risk stratification unit is indicative of whether the candidate is at-risk for one or more health conditions or has a propensity for complications with a diagnosed condition.

8. The system of claim 6, further comprising, an event router for routing the normalized health related data from the integration engine to the data storage element, a plurality of service modules each of which is configured for processing a different portion of the normalized health related data stored in the data storage element, and a query unit for generating a query and then searching the normalized health related data stored in the data storage element for one or more portions of the normalized health related data that satisfy the query.

9. The system of claim 6, further comprising a plurality of service modules each of which is configured for processing a different portion of the normalized health related data stored in the data storage element, wherein the plurality of service modules includes two or more of:

a scheduling service module for processing a scheduling event data portion of the normalized health related data, a clinical summary service module for processing a clinical summary event data portion of the normalized health related data, a clinical administration service module for processing an administration event data portion of the normalized health related data, and a clinical result service module for processing a test result portion of the normalized health related data.

10. A method for identifying a plurality of candidates for one or more clinical trials, comprising receiving health related data associated with each of the plurality of candidates, applying a predictive risk model to the health related data to generate and assign a risk score to each of the plurality of candidates based on a selected condition and to rank each of the plurality of candidates based on the risk score, wherein the predictive risk model comprises one or more trained risk models including at least one of a neural network model, a random forest model, a generalized linear model, a gradient boosted classifier model, a K-means clustering model, or a time series forecasting model, and generating a similarity score for each of the candidates having an assigned risk score higher than the threshold risk score with a matching machine learning technique, wherein the similarity score is indicative of a similarity between each of the plurality of candidates and one or more participants in the one or more clinical trials, wherein the machine learning technique includes a tensor factorization technique that decomposes a tensor into factor matrices storing information encoded in the tensor, wherein the similarity score is determined based on the information in the factor matrices, and wherein the similarity score is an average of values in the factor matrices.

11. The system of claim 10, wherein the scheduling service module generates a request for a query to a query unit based on the scheduling event data portion of the normalized health related data, and wherein in response to the request the query unit requests updated clinical summary event data from the one or more data sources.

12. The method of claim 10, wherein the health related data includes scheduling data indicative of a medical appointment and clinical summary data indicative of medical history data of each of the plurality of candidates, and wherein the risk score is generated based on at least the scheduling data and the medical history data.

13. The method of claim 10, further comprising comparing the risk score assigned to each of the plurality of candidates with a threshold level risk score, and identifying the candidates with risk scores above the threshold level.

14. The method of claim 13, further comprising applying one or more workflow rules to each of the plurality of candidates, and receiving evaluation data about one or more of the plurality of candidates having the assigned risk score above the threshold risk score level, wherein the evaluation includes additional health related data.

15. The method of claim 14, further comprising matching each of the candidates to one or more clinical trials based on the evaluation data and based on the risk score data.

16. The method of claim 15, further comprising determining, based on the assigned risk scores of each of the candidates, which of the candidates are to be evaluated.

17. The method of claim 16, further comprising ranking each of the plurality of candidates based on the similarity scores of the plurality of candidates.

18. The method of claim 17, further comprising generating the similarity score for each of the identified candidates based on the risk score and the evaluation data.

19. A non-transitory, computer readable medium comprising computer program instructions tangibly stored on the computer readable medium, wherein the computer program instructions are executable by at least one computer processor to perform a method, the method comprising:
receiving health related data associated with each of the plurality of candidates,
applying a predictive risk model to the health related data to generate and assign a risk score to each of the plurality of candidates based on a selected condition and to rank each of the plurality of candidates based on the risk score, wherein the predictive risk model comprises one or more trained risk models including at least one of a neural network model, a random forest model, a generalized linear model, a gradient boosted classifier model, a K-means clustering model, or a time series forecasting model, and
generating a similarity score for each of the candidates having an assigned risk score higher than the threshold risk score with a matching machine learning technique, wherein the similarity score is indicative of a similarity between each of the plurality of candidates and one or more participants in the one or more clinical trials,
wherein the machine learning technique includes a tensor factorization technique that decomposes a tensor into factor matrices storing information encoded in the tensor, wherein the similarity score is determined based on the information in the factor matrices, and wherein the similarity score is an average of values in the factor matrices.

20. The computer readable medium of claim 19, wherein the health related data includes scheduling data indicative of a medical appointment and clinical summary data indicative of medical history data of each of the plurality of candidates, and wherein the risk score is generated based on at least the scheduling data and the medical history data.

21. The computer readable medium of claim 19, further comprising comparing the risk score assigned to each of the plurality of candidates with a threshold level risk score, and identifying the candidates with risk scores above the threshold level.

22. The computer readable medium of claim 20, further comprising
applying one or more workflow rules to each of the plurality of candidates, and
receiving evaluation data about each of the plurality of candidates, wherein the evaluation includes additional health related data.

23. The candidate identification system of claim 1, wherein the predictive risk model comprises the gradient boosted classifier model, and wherein the gradient boosted classifier model is configured to generate the risk score for each candidate.

24. The candidate identification system of claim 23, wherein the predictive risk model is trained to a specific condition and a condition risk score is provided for each candidate for the specific condition.

25. The candidate identification system of claim 1, wherein the predictive risk model is continuously retrained based on outputs of the predictive risk model.

26. The candidate identification system of claim 1, wherein the one or more matching machine learning techniques are trained based on populations of patients that have successfully passed screening for clinical trials.

27. The candidate identification system of claim 26, wherein the one or more matching machine learning techniques include at least one of collaborative filtering, content-based filtering, similarity search, nearest-neighbors search, or matrix factorization.

28. The candidate identification system of claim 1, wherein the factor matrices comprise information associated with at least one of demographic information, problem and diagnosis history, body and biological measurement and vital history information, lab and test result history information, medical procedure history, medication history, social history, evaluation results, visits, procedures, or time between medical events.

29. The candidate identification system of claim 1, wherein a model deployed by the matching unit is continuously retrained based on outputs of the model.

* * * * *